United States Patent
Boubes

(10) Patent No.: US 11,819,645 B2
(45) Date of Patent: Nov. 21, 2023

(54) CATHETER AND METHOD OF USING A CATHETER

(71) Applicant: Khaled Boubes, Dublin, OH (US)

(72) Inventor: Khaled Boubes, Dublin, OH (US)

(*) Notice: Subject to any disclaimer, the term of this patent is extended or adjusted under 35 U.S.C. 154(b) by 714 days.

(21) Appl. No.: 16/798,376

(22) Filed: Feb. 23, 2020

(65) Prior Publication Data

US 2020/0269024 A1   Aug. 27, 2020

Related U.S. Application Data

(60) Provisional application No. 62/810,413, filed on Feb. 26, 2019.

(51) Int. Cl.
*A61M 25/10* (2013.01)
*A61M 25/00* (2006.01)
*A61M 39/02* (2006.01)

(52) U.S. Cl.
CPC .... *A61M 25/10182* (2013.11); *A61M 25/005* (2013.01); *A61M 25/0026* (2013.01); *A61M 39/0247* (2013.01); *A61M 2025/1043* (2013.01)

(58) Field of Classification Search
CPC ........ A61M 25/10182; A61M 25/0026; A61M 25/005; A61M 39/0247; A61M 2025/1043
USPC ...................................................... 604/97.02
See application file for complete search history.

(56) References Cited

U.S. PATENT DOCUMENTS

| | | | | |
|---|---|---|---|---|
| 4,762,130 A * | 8/1988 | Fogarty | ............. | A61M 25/0125 604/908 |
| 5,807,329 A * | 9/1998 | Gelman | ............. | A61M 25/0026 604/102.03 |
| 2003/0014008 A1 * | 1/2003 | Jacques | ............. | A61M 25/0032 600/431 |
| 2011/0092876 A1 * | 4/2011 | Bailey | ............. | A61M 25/10 604/6.16 |
| 2012/0029509 A1 * | 2/2012 | Smith | ............. | A61B 18/1492 606/41 |

(Continued)

OTHER PUBLICATIONS

Notification of Transmittal of the International Search Report and Written Opinion of the International Searching Authority, or the Declaration for International Application No. PCT/US2020 1019388, dated Jun. 15, 2020, pp. 1-12.

*Primary Examiner* — Phillip A Gray
(74) *Attorney, Agent, or Firm* — Nancy R. Gamburd; Gamburd Law Group LLC

(57) ABSTRACT

Representative embodiments of a catheter, e.g., a dialysis catheter, and a method of use of the catheter, are disclosed. A representative catheter includes a catheter body and a balloon coupled to the catheter body. The catheter body includes first, second, and third ports, with the second port arranged spaced apart longitudinally from the first port; and first, second, and third lumens, the first lumen in fluid communication with the first port, the second lumen in fluid communication with the second port, and the third lumen in fluid communication with the third port. The balloon is arranged between the first and second ports, and is coupled to the third port. The balloon is inflatable using a fluid injected through a connecting tube and into the third lumen, helping to remove any fibrin sheath which may have formed around the first and second ports, and diminish recirculation of blood during dialysis.

16 Claims, 8 Drawing Sheets

(56) References Cited

U.S. PATENT DOCUMENTS

2014/0081200 A1* 3/2014 Pruitt ................ A61M 25/1025
 604/103
2017/0157367 A1* 6/2017 Rusnak ............... A61M 1/3661

* cited by examiner

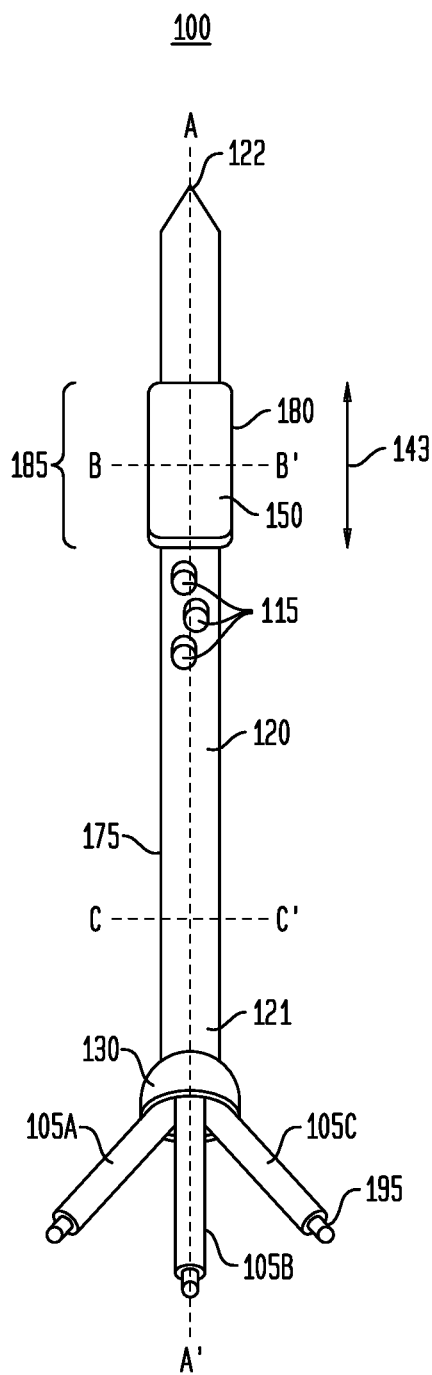
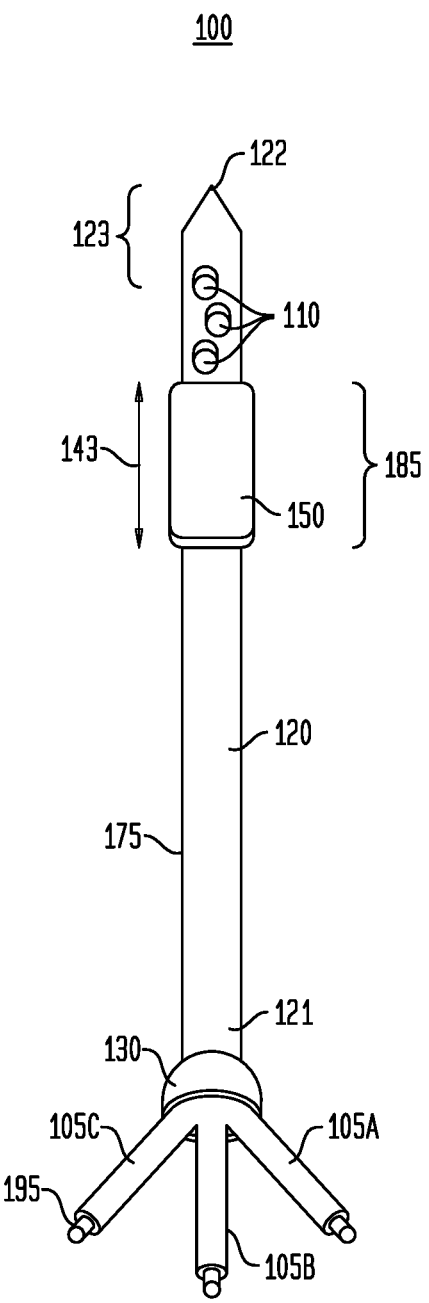
FIG. 1
FIG. 2

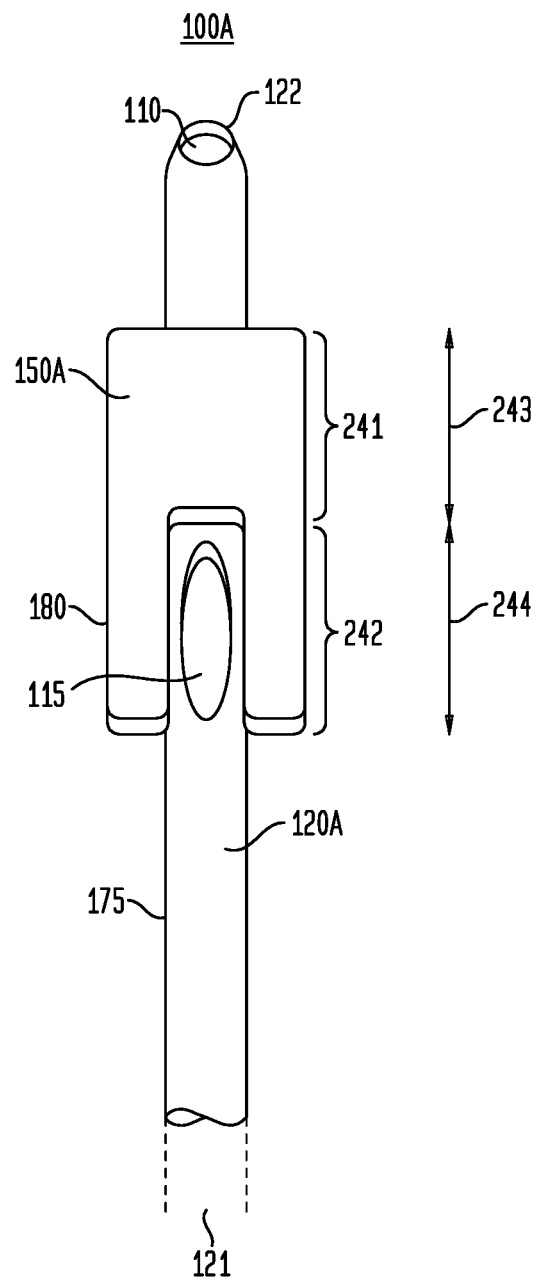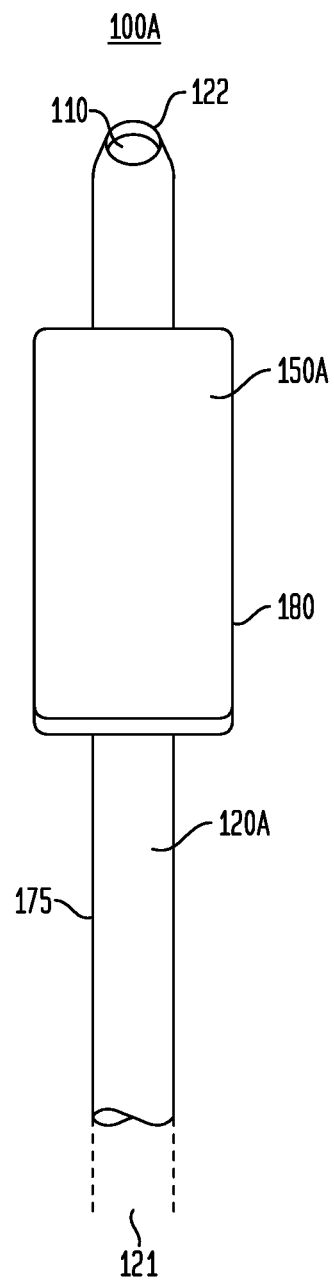

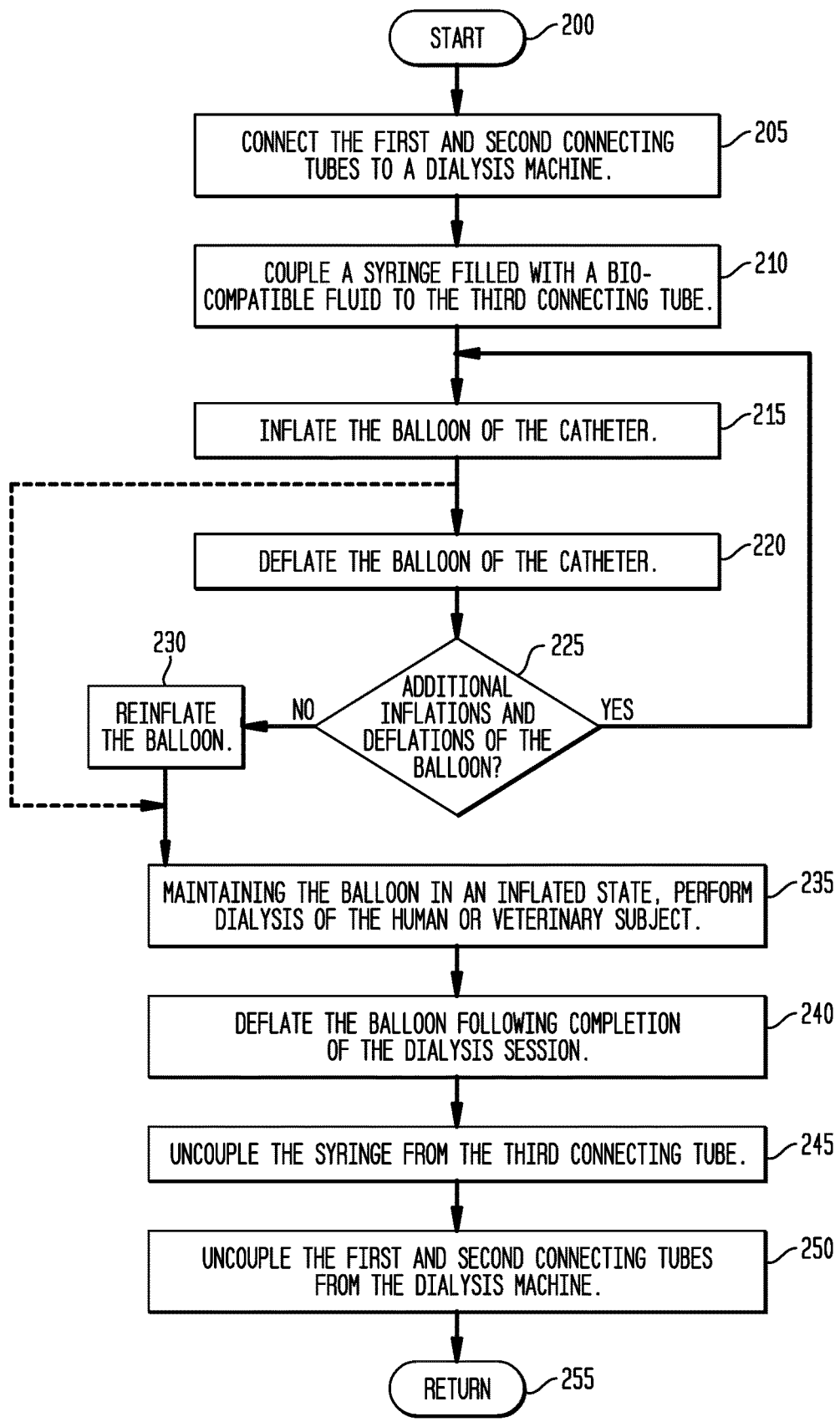

CATHETER AND METHOD OF USING A CATHETER

CROSS-REFERENCE TO A RELATED APPLICATION

This application is a nonprovisional of and claims the benefit of and priority to U.S. Provisional Patent Application No. 62/810,413, filed Feb. 26, 2019, inventor Khaled Boubes, titled "Dialysis Catheter and Method", and all of which is hereby incorporated herein by reference in its entirety with the same full force and effect as if set forth in its entirety herein.

FIELD OF THE INVENTION

The present invention, in general, relates to catheters and, more specifically, relates to a dialysis catheter having a balloon and a method of using the dialysis catheter.

BACKGROUND OF THE INVENTION

Central dialysis catheters are utilized in about twenty percent of patients undergoing dialysis, typically about 80,000 patients in the United States at any given time. In a surgical procedure, a dialysis catheter is inserted into a large vein of the patient, with the ports of the dialysis catheter typically positioned in the superior vena cava, and with connecting tubes positioned outside the patient for coupling to a dialysis machine. One of the ports (with a corresponding interior lumen of the catheter) is utilized to withdraw blood from the patient and provide it to a dialysis machine (often referred to as an arterial port and lumen), and the other port (with a corresponding interior lumen of the catheter) is utilized to return blood to the patient from the dialysis machine (often referred to as a venous port and lumen).

Most dialysis patients initially receive a dialysis catheter to have dialysis procedures while they are in the process of receiving and healing from a surgically constructed fistula or graft connecting an artery and a vein, typically in one of the patient's arms, as a radiocephalic arteriovenous fistula. Once the fistula or graft is healed and ready for use in dialysis, the dialysis catheter is typically removed. In the event that the fistula or graft becomes injured or otherwise problematic, another dialysis catheter may be reinserted and utilized for dialysis instead of using the fistula or graft.

Complications may arise, however, from this use of dialysis catheters. Clinically, fibrin sheath formation on dialysis catheters is a common problem due to the human body's response to a foreign object. Fibrin sheath formation may cover the catheter ports of a dialysis catheter, blocking or reducing blood flow, rendering the dialysis catheter less efficient or completely nonfunctional. Fibrin sheath formation has been reported to significantly reduce patency of the dialysis catheter, with reports of primary patency of only 42% at 60 days and 16% at 120 days, and secondary patency of 92% at 60 days and 82% at 120 days.

Current methods of addressing fibrin sheath formation typically require surgical intervention or additional medical procedures, such as replacement of the dialysis catheter or insertion of a snare to strip the fibrin sheath from the catheter, typically in another surgical procedure. Risks of additional complications, such as infection, are also incurred with repetitive removal and replacement of the dialysis catheter.

In addition, recirculation of blood is a common problem with many current dialysis catheters. Such recirculation occurs when some of the dialyzed (or cleansed) blood exiting an output port of a dialysis catheter is virtually immediately returned via an input port to the dialysis catheter and back to the dialysis machine, further reducing the efficiency of dialysis and thereby requiring longer dialysis sessions.

Movement of the dialysis catheter during dialysis sessions may also be problematic. For example, the intake of blood through an intake port may create a suction force, and in some circumstances, this suction may cause the intake port to adhere to or abut the blood vessel wall, blocking or partially blocking the intake port and, again, further reducing the efficiency of dialysis and thereby requiring longer dialysis sessions or medical intervention during a dialysis session.

A need remains, therefore, for a dialysis catheter and method of using the dialysis catheter which reduces the likelihood of formation of a fibrin sheath which blocks the catheter ports. Such a dialysis catheter should be comparatively easy for medical personnel to use. In addition, such a dialysis catheter should prevent or diminish blood recirculation, and further, should reduce the likelihood of blockage of the ports of the dialysis catheter due to the positioning or adhering of the catheter to a vessel wall.

SUMMARY OF THE INVENTION

The exemplary or representative embodiments of the present invention provide numerous advantages. Various representative embodiments provide a catheter, such as a dialysis catheter, and a method of using the catheter for dialysis which reduces the likelihood of formation of a fibrin sheath that might block the catheter ports. The representative embodiments of such a catheter are comparatively easy for medical personnel to use for dialysis. In addition, representative embodiments of such a catheter prevent or diminish blood recirculation during dialysis, and further, reduce the likelihood of blockage of the ports of the catheter due to the positioning or adhering of the catheter to a vessel wall.

In a representative embodiment, a catheter, such as a dialysis catheter, may comprise: a catheter body and a balloon, coupled to the catheter body. The catheter body has a first end and a second end, with the catheter body comprising: a plurality of ports, the plurality of ports comprising at least one first port, at least one second port, and at least one third port, the at least one first port arranged at or spaced apart from the first end, the at least one second port arranged spaced apart longitudinally from the at least one first port; and a plurality of lumens, the plurality of lumens comprising a first lumen, a second lumen, and a third lumen, the first lumen in fluid communication with the at least one first port, the second lumen in fluid communication with the at least one second port, and the third lumen in fluid communication with the at least one third port.

In a representative embodiment, the balloon comprises a balloon lumen, and the balloon is coupled to the at least one third port, with the third lumen in fluid communication with the third port and the balloon lumen.

In a representative embodiment, the balloon may be at least partially surrounding the catheter body and is coupled to the catheter body in between the at least one first port and the at least one second port.

In a representative embodiment, a diameter of the balloon in an inflated state may be user-selectable. In a representative embodiment, the balloon comprises a biocompatible material.

In a representative embodiment, the balloon may be coupled at a first location of the catheter body, the first location extending longitudinally a first predetermined distance between the at least one first port and the at least one second port. In a representative embodiment, the balloon may be at least partially surrounding the catheter body and is coupled to the catheter body at a first location in between the at least one first port and the at least one second port. In such a representative embodiment, the balloon may be coupled circumferentially at the first location.

In a representative embodiment, the balloon may be further coupled at a second location of the catheter body, the second location at least partially surrounding the at least one second port. In another representative embodiment, the balloon may be further coupled at a second location of the catheter body, the second location extending longitudinally a second predetermined distance to partially surround the at least one second port. In another representative embodiment, the balloon may be further coupled at a second location of the catheter body, the second location extending longitudinally a second predetermined distance between the at least one second port and the second end. In another representative embodiment, the balloon may be coupled helically around the catheter body at the second location.

In another representative embodiment, when the balloon is in an inflated state, the balloon comprises a first diameter at the first location and a second diameter at the second location, the first diameter greater than the second diameter. In a representative embodiment, for example, the first diameter at the first location may progressively narrow to the second diameter at the second location.

In a representative embodiment, the at least one first port and the at least one second port may be offset transversely and arranged on opposite sides of the catheter body.

In a representative embodiment, a catheter, such as a dialysis catheter, may further comprise: a hub coupled to the second end of the catheter body; and a plurality of connecting tubes coupled to the hub, the plurality of connecting tubes comprising a first connecting tube in fluid communication with the first lumen, a second connecting tube in fluid communication with the second lumen, and a third connecting tube in fluid communication with the third lumen. In another representative embodiment, the third connecting tube may be configured with a connector to mate with a luer lock tip of a syringe.

A representative embodiment of a method of using a representative embodiment of a catheter, such as a dialysis catheter, is also disclosed, with the catheter having been inserted into a blood vessel of a human or veterinary subject. In such a representative embodiment, the method may comprise: coupling the first and second connecting tubes to a dialysis machine; inflating the balloon of the catheter; and while the balloon is inflated, performing dialysis of the human or veterinary subject.

In a representative embodiment, the method of using the catheter may further comprise: prior to performing dialysis, repeatedly inflating and deflating the balloon. In a representative embodiment, after performing dialysis of the human subject, the method may further comprise: deflating the balloon of the catheter; and disconnecting the first and second connecting tubes from the dialysis machine In a representative embodiment, the step of inflating the balloon may further comprise: coupling a syringe to the third connecting tube, the syringe filled with a biocompatible fluid; and using the syringe, injecting the biocompatible fluid into the third connecting tube to inflate the balloon.

In another representative embodiment, a catheter, such as a dialysis catheter, may comprise: a catheter body and a balloon, coupled to the catheter body. The catheter body has a first end and a second end, with the catheter body comprising: a plurality of ports, the plurality of ports comprising at least one first port, at least one second port, and at least one third port, the at least one first port arranged at or spaced apart from the first end, the at least one second port arranged spaced apart from the at least one first port; and a plurality of lumens, the plurality of lumens comprising a first lumen, a second lumen, and a third lumen, the first lumen in fluid communication with the at least one first port, the second lumen in fluid communication with the at least one second port; and the balloon has a balloon lumen, the balloon coupled to the catheter body at a first location between the at least one first port and the at least one second port, the balloon further coupled to the at least one third port, with the third lumen in fluid communication with the at least one third port and the balloon lumen.

In another representative embodiment, the balloon may be further coupled helically around the catheter body at a second location between the at least one second port and the second end of the catheter body. In another representative embodiment, the at least one first port and the at least one second port may be offset transversely and arranged on opposite sides of the catheter body.

In a representative embodiment, a catheter, such as a dialysis catheter, may comprise: a catheter body and a helical balloon, coupled to the catheter body. The catheter body has having a first end and a second end, with the catheter body comprising: a plurality of ports, the plurality of ports comprising at least one first port, at least one second port, and at least one third port, the at least one first port arranged at or spaced apart from the first end on a first side of the catheter body, the at least one second port arranged spaced apart longitudinally from the at least one first port and the at least one second port arranged spaced apart transversely from the at least one first port on a second, opposite side of the catheter body; and a plurality of lumens, the plurality of lumens comprising a first lumen, a second lumen, and a third lumen, the first lumen in fluid communication with the at least one first port, the second lumen in fluid communication with the at least one second port; and the helical balloon has a balloon lumen, the helical balloon coupled to the catheter body at a first location between the at least one first port and the at least one second port, the helical balloon further coupled helically around the catheter body at a second location between the at least one second port and the second end of the catheter body, the helical balloon further coupled to the at least one third port, with the third lumen in fluid communication with the at least one third port and the balloon lumen.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIG. 1 is a first isometric view illustrating a representative first embodiment of a catheter, such as a dialysis catheter, having a representative first embodiment of a balloon in a first, uninflated or deflated state or configuration.

FIG. 2 is a second isometric view illustrating the representative first embodiment of the catheter having the representative first embodiment of the balloon in the first, uninflated or deflated state or configuration.

FIG. 10 is a first, partial isometric view illustrating a representative second embodiment of a catheter, such as a dialysis catheter, having a representative second embodiment of a balloon in a second, inflated state or configuration.

FIG. 11 is a second, partial isometric view illustrating the representative second embodiment of the catheter having the representative second embodiment of the balloon in the second, inflated state or configuration.

FIG. 17 is a flow chart illustrating a method of using a representative embodiment of a catheter, such as a dialysis catheter, having a representative embodiment of a balloon during a dialysis session.

DETAILED DESCRIPTION OF REPRESENTATIVE EMBODIMENTS

Figure 3:
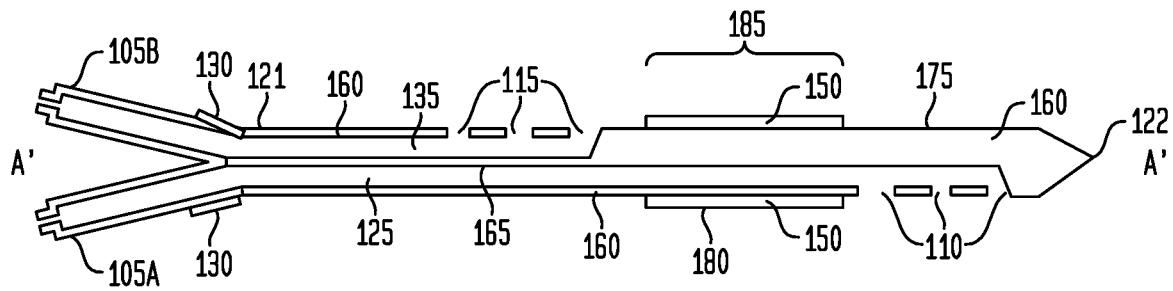
FIG. 3 is longitudinal (and sagittal), cross-sectional view (in the A-A' plane) illustrating the representative first embodiment of the catheter having the representative first embodiment of the balloon in the first, uninflated or deflated state or configuration of FIG. 1.

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

As mentioned above, various representative embodiments provide a catheter, such as a dialysis catheter, and a method of using the catheter which reduces the likelihood of formation of a fibrin sheath that might block the catheter ports. The representative embodiments of such a catheter are comparatively easy for medical personnel to use, such as for dialysis. In addition, representative embodiments of such a catheter prevent or diminish blood recirculation during dialysis, and further, reduce the likelihood of blockage of the ports of the catheter due to the positioning or adhering of the catheter to a vessel wall.

While the representative embodiments of such a catheter 100, 100A, 100B are primarily focused upon use the catheter 100, 100A, 100B for dialysis, and thus may be considered to be dialysis catheters 100, 100A, 100B, those having skill in the art will recognize that such a catheter 100, 100A, 100B may have other or additional medical, surgical, or veterinary applications, in addition to dialysis applications.

Figure 4:
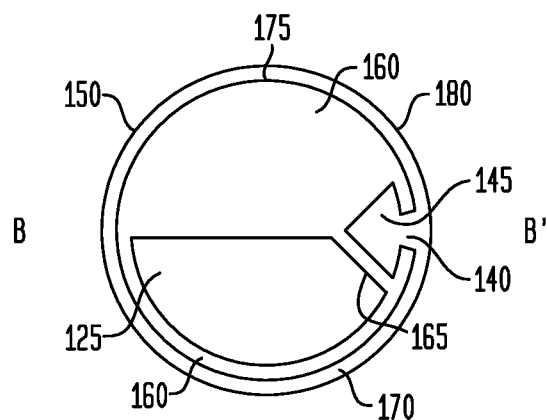
FIG. 4 is a first, transverse cross-sectional view (in the B-B' plane) illustrating the representative first embodiment of the catheter having the representative first embodiment of the balloon in the first, uninflated or deflated state or configuration of FIG. 1.
Figure 5:
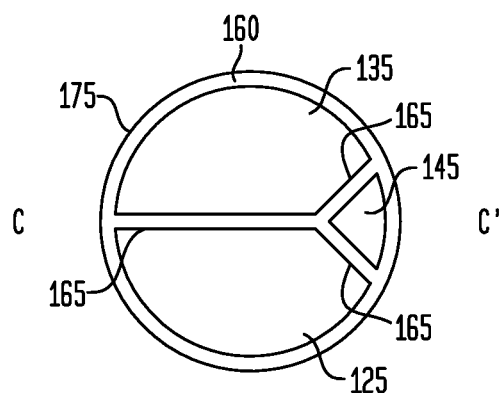
FIG. 5 is a second, transverse cross-sectional view (in the C-C' plane) illustrating the representative first embodiment of the catheter having the representative first embodiment of the balloon in the first, uninflated or deflated state or configuration of FIG. 1.
Figure 6:
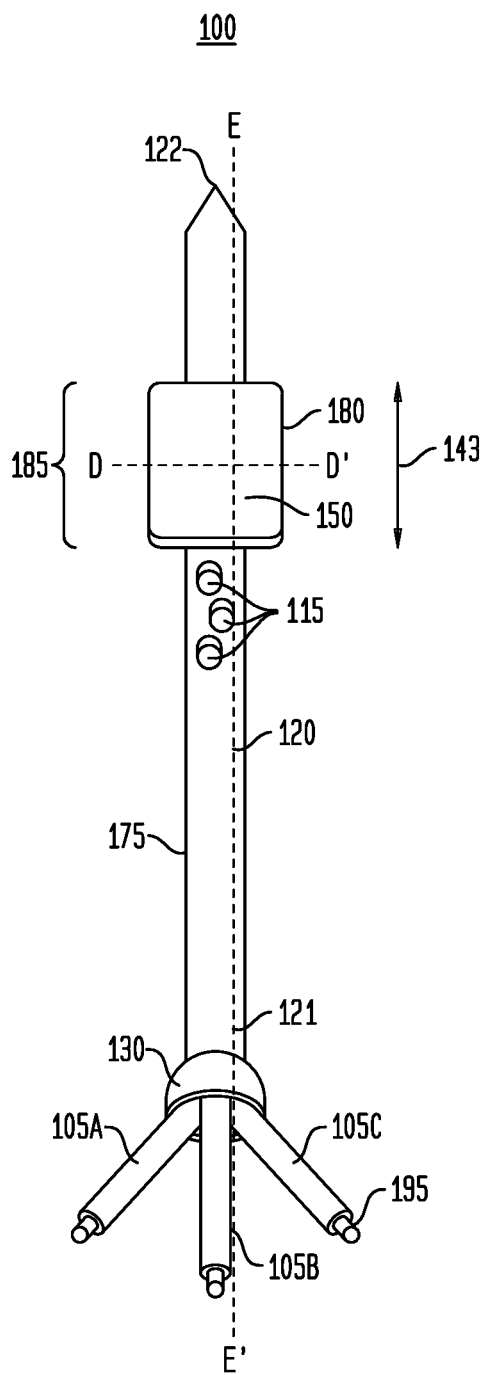
FIG. 6 is a first isometric view illustrating the representative first embodiment of the catheter having the representative first embodiment of the balloon in a second, inflated state or configuration.
Figure 7:
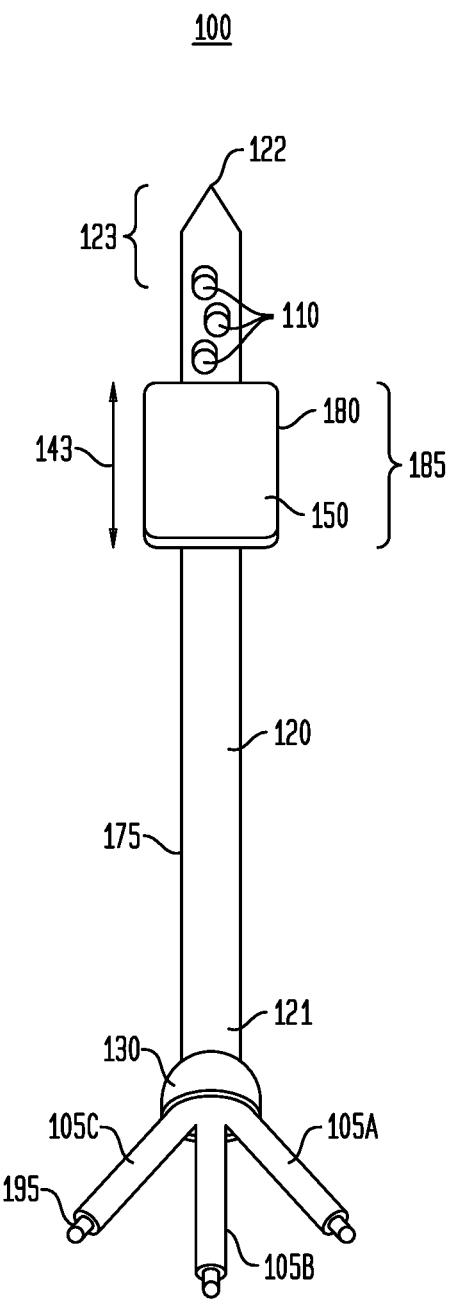
FIG. 7 is a second isometric view illustrating the representative first embodiment of the catheter having the representative first embodiment of the balloon in the second, inflated state or configuration.
Figure 8:
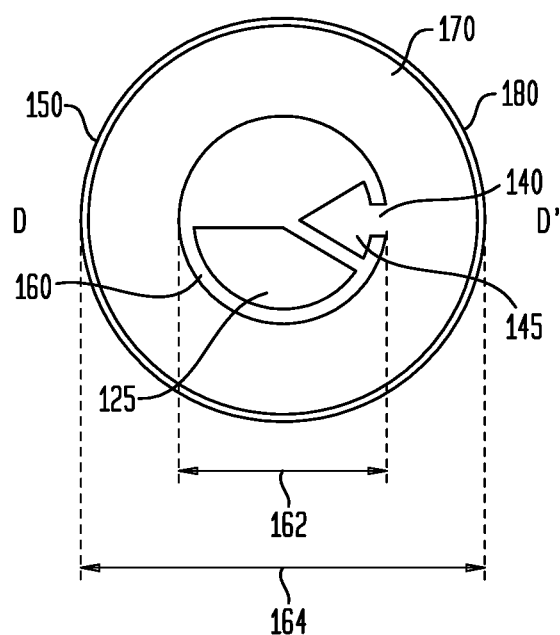
FIG. 8 is a transverse cross-sectional view (in the D-D' plane) illustrating the representative first embodiment of the catheter having the representative first embodiment of the balloon in the in the second, inflated state or configuration of FIG. 7.
Figure 9:
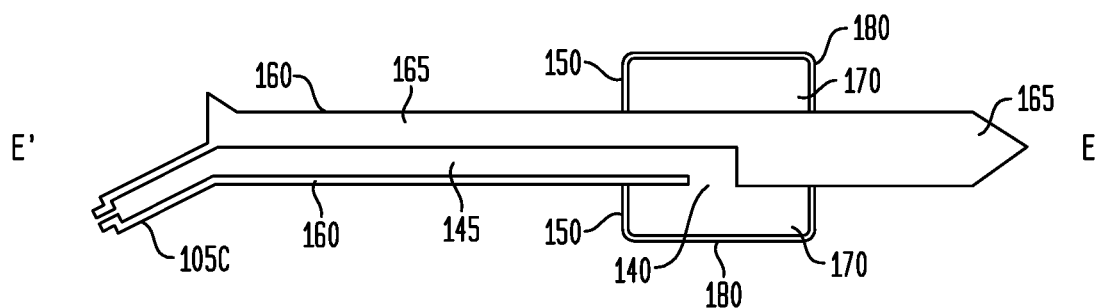
FIG. 9 is a coronal cross-sectional view (in the E-E' plane) illustrating the representative first embodiment of the catheter having the representative first embodiment of the balloon in the in the second, inflated state or configuration of FIG. 7.

FIG. 1 is a first (anterior) isometric view illustrating a representative first embodiment of a catheter 100, such as a dialysis catheter, having a representative first embodiment of a balloon 150 in a first, uninflated or deflated state or configuration. FIG. 2 is a second (posterior) isometric view illustrating the representative first embodiment of the catheter 100 having the representative first embodiment of the balloon 150 in the first, uninflated or deflated state or configuration. FIG. 3 is longitudinal, cross-sectional view (in the A-A' plane) illustrating the representative first embodiment of the catheter 100 having the representative first embodiment of the balloon 150 in the first, uninflated or deflated state or configuration of FIG. 1. FIG. 4 is a first, transverse cross-sectional view (in the B-B' plane) illustrating the representative first embodiment of the catheter 100 having the representative first embodiment of the balloon 150 in the first, uninflated or deflated state or configuration of FIG. 1. FIG. 5 is a second, transverse cross-sectional view (in the C-C' plane) illustrating the representative first embodiment of the catheter 100 having the representative first embodiment of the balloon 150 in the first, uninflated or deflated state or configuration of FIG. 1. FIG. 6 is a first (anterior) isometric view illustrating the representative first embodiment of the catheter 100 having the representative first embodiment of the balloon 150 in a second, inflated state or configuration. FIG. 7 is a second (posterior) isometric view illustrating the representative first embodiment of the catheter 100 having the representative first embodiment of the balloon 150 in the second, inflated state or configuration. FIG. 8 is a transverse cross-sectional view (in the D-D' plane) illustrating the representative first embodiment of the catheter 100 having the representative first embodiment of the balloon 150 in the in the second, inflated state or configuration of FIG. 7. FIG. 9 is a coronal cross-sectional view (in the E-E' plane, orthogonal to the sagittal A-A' plane of FIGS. 1 and 3) illustrating the representative first embodiment of the catheter 100 having the representative first embodiment of the balloon 150 in the in the second, inflated state or configuration of FIG. 7.

It should also be noted that, unless the context otherwise indicates, reference to any one of the catheters 100, 100A, 100B (100-100B) described below and their components or configurations shall be understood to mean and include any other catheters 100-100B and its components or configurations, reference to any one of the catheter bodies 120, 120A described below and their components or configurations shall be understood to mean and include any other catheter body 120, 120A, 120B (120-120B) and its components or configurations, and reference to any one of the balloons 150, 150A, 150B (150-150B) described below and their components or configurations shall be understood to mean and include any other balloons 150-150B and its components or configurations, without limitation.

For ease of reference, directions and orientations utilized herein are with reference to the lengthwise axis of the catheter 100-100B, as the longitudinal dimension, with the radial dimension extending radially (or outwards) from the lengthwise axis of the catheter 100-100B, and with the transverse dimension being orthogonal to the longitudinal dimension, e.g., across the width of the catheter 100-100B, as will be apparent to those having skill in the art from the following disclosure, for example, the transverse dimension being east or west to a north-south longitudinal dimension.

Referring to FIGS. 1-9, a catheter 100, such as a dialysis catheter, comprises a catheter body 120, a balloon 150, a hub 130, and a plurality of connecting tubes 105, illustrated as a first connecting tube 105A, a second connecting tube 105B, and a third connecting tube 105C. The catheter body 120-120B comprises a first, distal end 122 and a second, proximal end 121. The first, distal end 122 can be inserted into a blood vessel of a human subject, as previously discussed. The second, proximal end 121 is coupled to the hub 130, and either or both of which remain outside the patient (such as a human or veterinary subject) when the catheter 100 has been placed inside the patient or other subject. The first connecting tube 105A and second connecting tube 105B are coupleable (typically through additional tubing, not separately illustrated) to a dialysis machine (also not separately illustrated). The hub 130 is coupled to the first connecting tube 105A, such as for blood removal from a patient for provision to the dialysis machine, and coupled to the second connecting tube 105B, such as for returning blood to the patient from the dialysis machine (or vice-versa). The hub 130 is coupled to the third connecting tube 105C, which is coupleable to a syringe (not separately illustrated), for example, which is typically filled with a biocompatible fluid such as saline, also example and without limitation, and utilized for inflating and deflating the balloon 150, as discussed in greater detail below. In representative embodiments, the third connecting tube is configured with a mating luer lock connector 195 to mate with a luer lock tip of a syringe for the injection and withdrawal of the biocompatible fluid.

The first, distal end 122 of the catheter body 120, 120A, 120B can be any shape, in addition to the illustrated conical shape for catheter body 120, 120B, such as a columnar or an irregular shape, provided that the first, distal end 122 can be inserted into a blood vessel of a human subject. The distal end 122 is illustrated as pointed in FIGS. 2, 3, 7, and 12, as an example and without limitation. The one or more first ports 110 can be arranged spaced apart, such as by a predetermined distance 123, from the first, distal end 122 of the catheter body 120, 120B as illustrated in FIGS. 2, 3, 7, and 12, or the one or more first ports 110 can be arranged directly at the first, distal end 122 of the catheter body 120A as illustrated in FIGS. 10 and 11. The catheter body 120, 120A, 120B The balloons 150-150B can be made of any biocompatible, flexible material, as known or becomes known in the art, such as silicone, latex, or any of the other materials described below. A balloon 150-150B may be coupled or otherwise connected to and sealed against the catheter body 120, 120A, 120B as known or becomes known in the art. For example and without limitation, a balloon 150-150B may be integrally formed with the catheter body 120, 120A, 120B, or the balloon may be coupled or otherwise connected to and sealed against the catheter body 120, 120A, 120B such as through an adhesive or welding. While each of the various representative embodiments of the catheters 100, 100A, 100B are illustrated as having only a single balloon 150-150B, those having skill in the art will recognize that multiple balloons 150-150B may be utilized equivalently, each coupled to a third port 140, and all such variations are considered equivalent and within the scope of the disclosure.

The catheter body 120, 120A, 120B is generally elongated and cylindrical, typically circular overall in cross section as illustrated, although it may have any suitable shape or configuration, in addition to those illustrated, and is sized or configured for insertion into a blood vessel. The catheter body 120, 120A, 120B may comprise any biocompatible, flexible material, as known or becomes known in the art. The catheter body 120, 120A, 120B comprises a plurality of lumens (or channels) extending longitudinally, illustrated as a first lumen 125, a second lumen 135, and a third lumen 145, and a plurality of ports, illustrated as one or more first ports 110, one or more second ports 115, and one or more third ports 140. The one or more first ports 110, the one or more second ports 115, and the one or more third ports 140 are openings, apertures, or holes in an outer wall 160 of the catheter body 120, and can have any suitable size, shape or configuration. The plurality of lumens (or channels), illustrated as a first lumen 125, a second lumen 135, and a third lumen 145, may have any suitable size, shape or configuration, and are separated from each other by an internal septum 165, which also may have any suitable size, shape or configuration.

The one or more first ports 110 are in fluid communication, via the first lumen 125 with the first connecting tube 105A, and the one or more second ports 115 are in fluid communication, via the second lumen 135, with the second connecting tube 105B. It should be noted that the one or more first ports 110, the one or more second ports 115, and the one or more third ports 140 may have any number of ports, in addition to or fewer than the number of ports illustrated, for example and without limitation. In addition, the one or more first ports 110 and the one or more second ports 115 may have any of a plurality of locations on the catheter body 120. For example and without limitation, in a representative embodiment, the one or more first ports 110 and the one or more second ports 115 are also offset transversely from each other and arranged on the opposite sides of the catheter body 120, 120B in the catheter 100, 100B, as illustrated in FIGS. 1-3, 6, 7, 12, and 13. In another representative embodiment, not separately illustrated, the one or more first ports 110 and the one or more second ports 115 are also offset longitudinally from each other but are arranged on the same side of a catheter body 120, 120A, 120B in a catheter 100, 100A, 100B.

The first lumen 125 is in fluid communication with the one or more first ports 110, and the second lumen 135 is in fluid communication with the one or more second ports 115. For example and without limitation, blood that will be dialyzed (filtered or cleansed) flows into the one or more first ports 110, then into the first lumen 125, and then into the first connecting tube 105A and on to a dialysis machine (not separately illustrated). Similarly, dialyzed (filtered or cleansed) blood flows from the second connecting tube 105B into and through the second lumen 135, then through the one or more second ports 115, and into the patient's blood vessel.

It should be noted that the various lumens 125, 135, 145 may or may not extend the entire length of the catheter body 120, 120A, 120B. For example, as illustrated in FIGS. 3, 4, 8, and 14, the second lumen 135 extends longitudinally within the interior of the catheter body 120, 120B only to and including the locations of the one or more second ports 115, and not further toward the first end 122, e.g., to avoid any pooling of blood toward the first end 122. For the sake of completeness, those having skill in the art will recognize that the second lumen 135 may extend further longitudinally within the interior of the catheter body 120, 120A, 120B, such as to additional second ports 115 (not separately illustrated), and all such variations are within the scope of the disclosure.

Figure 13:
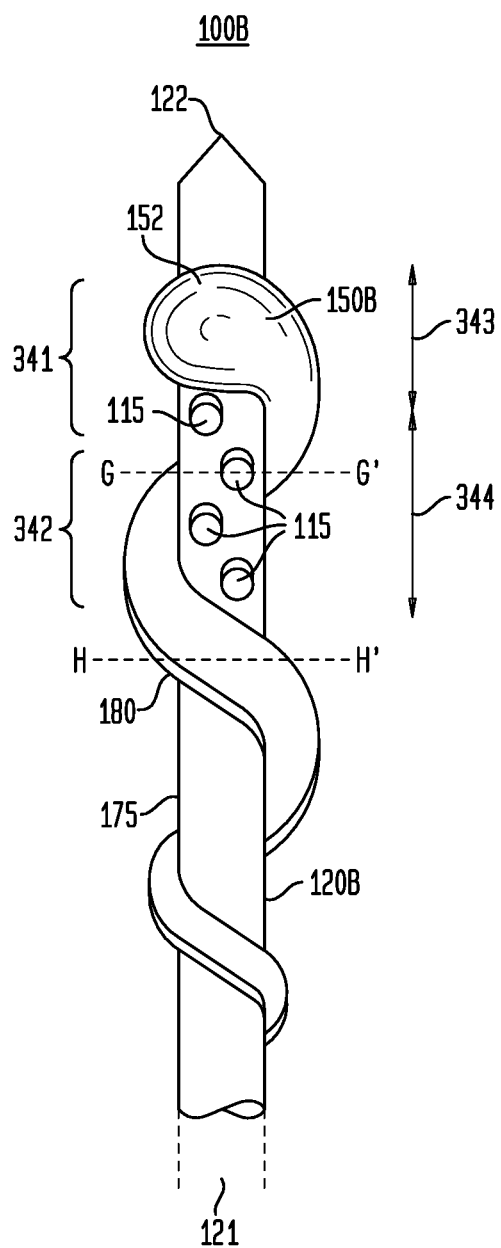
FIG. 13 is a second, partial isometric view illustrating the representative third embodiment of the catheter having the representative third embodiment of the balloon in the second, inflated state or configuration.
Figure 14:
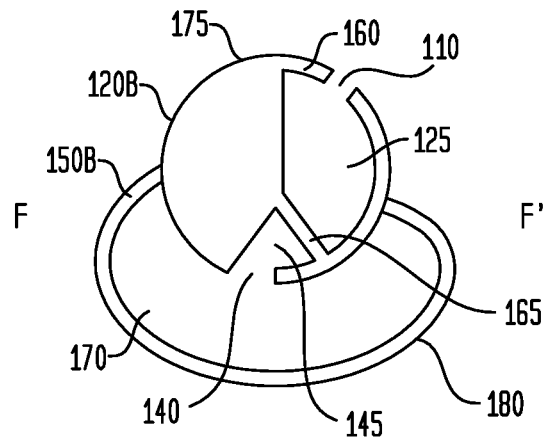
FIG. 14 is a first, transverse cross-sectional view (in the F-F' plane) illustrating the representative third embodiment of the catheter having the representative third embodiment of the balloon in the second, inflated state or configuration of FIG. 12.
Figure 15:
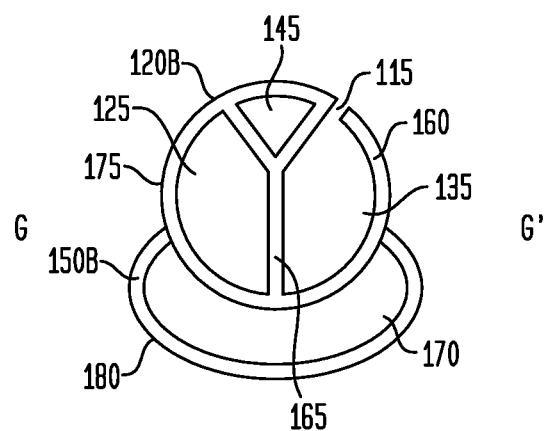
FIG. 15 is a second, transverse cross-sectional view (in the G-G' plane) illustrating the representative third embodiment of the catheter having the representative third embodiment of the balloon in the second, inflated state or configuration of FIG. 13.
Figure 16:
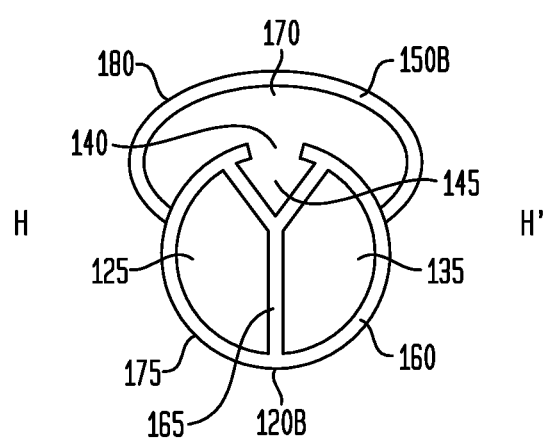
FIG. 16 is a third, transverse cross-sectional view (in the H-H' plane) illustrating the representative third embodiment of the catheter having the representative third embodiment of the balloon in the second, inflated state or configuration of FIG. 13.

A balloon 150-150B has or further comprises an interior, balloon lumen 170 and an exterior surface 180. The catheter body 120, 120A, 120B includes at least one third lumen 145, as an inflation and deflation lumen, and one or more third ports 140 which are in fluid communication with the third connecting tube 105C through the third lumen 145, and in fluid communication with the balloon lumen 170, to inflate and deflate the balloon 150-150B. The one or more third ports 140 is or are connected or contiguous with the third lumen 145. The third lumen 145, the one or more third ports 140, and the balloon lumen 170 are used to inflate and deflate the balloon 150-150B. The third lumen 145 is connected to the balloon lumen 170 via the one or more third ports 140, such as illustrated in FIGS. 4, 8, 9, 14, 15, and 16. A biocompatible fluid (not separately illustrated), such as saline, can be injected into the third connecting tube 105C and flow through third lumen 145, through the one or more third ports 140, and then into the balloon lumen 170, inflating the balloon 150-150B, as illustrated in FIGS. 6-16. The balloon 150-150B can be deflated using the syringe by withdrawing the biocompatible fluid, flowing from the balloon lumen 170 through the one or more third ports 140, the third lumen 145, and the third connecting tube 105C, into the syringe. This process of inflation and deflation may be repeated, as discussed below, to break up any fibrin sheath which may have formed. It should be noted that the catheter 100 may have any number of the third lumens 145 and third ports 140. One third lumen 145 and one third port 140 of a catheter body 120, 120A are illustrated in FIGS. 4, 5, 8, and 9, and multiple third ports 140 of a catheter body 120B are illustrated in FIGS. 14 and 16, as examples and without limitation. Based on the above structure, the biocompatible inflation fluid does not come into contact with the blood stream and remains in the balloon lumen 170 and the third lumen 145.

Referring to FIGS. 1-9, the balloon 150, as a first embodiment, is configured as a tube, or a hollow cylinder or a hollow torus, and is coupled circumferentially to the exterior surface 175 of the catheter wall 160 of the catheter body 120, i.e., is coupled at least partially around the circumference of the exterior surface 175 of the catheter body 120. As illustrated, the balloon 150 is arranged in a first location 185 of the catheter body 120 between the one or more first ports 110 and the one or more second ports 115, and the balloon 150 extends longitudinally and circumferentially between the one or more first ports 110 and the one or more second ports 115. The first location 185 extends longitudinally a first predetermined distance 143 between the one or more first ports 110 and the one or more second ports 115, and is a sufficient distance to not cover the one or more first ports 110 and the one or more second ports 115 when the balloon 150 is inflated. The problem of fibrin sheath formation will be mitigated after the balloon 150-150B is inflated or repeatedly inflated and deflated. Prior to or during a dialysis session, the balloon 150-150B can be inflated and deflated to break up any fibrin sheath which may have formed on the exterior surface 175 of the catheter body 120 and which may cover or otherwise affect the one or more first ports 110 and the one or more second ports 115. Specifically, a fibrin sheath may have formed on the exterior surface 175 of the catheter body 120 when the balloon 150-150B is deflated, such as in between dialysis sessions. After the balloon 150-150B is inflated, however, the inflated balloon 150-150B pushes or pulls on any overlying fibrin sheath and serves to break up the fibrin sheath, uncovering or cleaning the one or more first ports 110 and the one or more second ports 115. Therefore, any blockage of the one or more first ports 110 and the one or more second ports 115 can be prevented or mitigated.

In general, with dialysis sessions occurring several times per week, and with the balloon 150-150B being repeatedly inflated and deflated prior to each session to break up or remove any fibrin sheath which may have formed in between dialysis sessions, the formation of a substantial fibrin sheath which may block the one or more first ports 110 and the one or more second ports 115 is mitigated or eliminated. In addition, as any fibrin sheath which may have formed in between dialysis sessions will be comparatively small and thin, the pieces of fibrin sheath which are removed are also comparatively small and are rapidly dissipated and removed from the blood stream.

In representative embodiments, the balloon 150-150B is maintained in the second, inflated state during a dialysis session, operating as at least a partial barrier between the one or more first ports 110 and the one or more second ports 115. This serves to reduce the amount of recirculation during dialysis, as an additional benefit.

It should be noted that a diameter or size of the balloon 150-150B in an inflated state is user-selectable, provided the inflated balloon 150-150B can perform the functions described above. For example and without limitation, the depending upon the size of the balloon 150-150B when deflated, depending upon the material selected to comprise the balloon 150-150B, and depending upon the amount of biocompatible fluid injected by the user (such as medical personnel), e.g., 25 ml, 50 ml, etc., the inflated balloon 150-150B can have a wide range of sizes determined by the user. In addition, the inflated balloon 150 may have any shape. For example, the inflated balloon 150 is columnar or cylindrical in this first embodiment illustrated in FIGS. 1, 2, 6 and 7. The balloon 150 may have any suitable size, shape or configuration, such as a spherical shape, a U-shape, a helical shape, such as the balloons 150A, 150B, discussed below, for example and without limitation. In a representative embodiment, the catheter 100 has a first diameter 162, and the balloon 150 is inflated up to a second diameter 164, with the second diameter 164 being greater than the first diameter 162 and less than or equal to twice the first diameter 162 of the catheter 100, as illustrated in FIG. 8, for example and without limitation.

FIG. 10 is a first (anterior), partial isometric view illustrating a representative second embodiment of a catheter 100A, such as a dialysis catheter, having a representative second embodiment of a balloon 150A in a second, inflated state or configuration. FIG. 11 is a second (posterior), partial isometric view illustrating the representative second embodiment of the catheter 100A having the representative second embodiment of the balloon 150A in the second, inflated state or configuration. FIGS. 10 and 11 are shown as partial views of the catheter 100A, without illustrating the connecting tubes 105A, 105B, 105C, and the various lumens 125, 135, 145, because the catheter 100A includes the same connecting tubes 105A, 105B, 105C, and lumens 125, 135, 145 in the same configuration as previously described for catheter 100, and operates identically to the catheter 100, differing only with respect to the configuration and location of the balloon 150A, the configuration and location of the one or more first ports 110, and the configuration and location of the one or more second ports 115 as illustrated in the partial views. In the interests of brevity, only the differences between the catheter 100A and the catheter 100 are described.

Referring to FIGS. 10 and 11, the differences between the catheter 100A and the catheter 100 are: (1) the configuration of a balloon 150A, as a U-shaped balloon 150A (illustrated in FIG. 10), (2) the location of the balloon 150A on the catheter body 120A; (3) the configuration and location of the first port 110 at the first end 122 of the catheter body 120A, rather than multiple first ports 110 being spaced apart from the first end 122 of the catheter body 120; and (4) the configuration and location of the one or more second ports 115, as a single second port 115, rather than multiple second ports 115. Specifically, the balloon 150A is coupled circumferentially at a first location 241 of the catheter body 120A. The first location 241 extends longitudinally a first predetermined distance 243 between the first port 110 and the second port 115. The balloon 150A is further coupled at least partially surrounding the second port 115 at a second location 242 of the catheter body 120A. The second location 242 extends longitudinally a second predetermined distance 244 adjacent the second port 115. With the balloon 150A located at the second location 242, any blockage of the second port 115 can be further mitigated or removed, and the catheter 100A is operated as previously discussed with reference to catheter 100. The inflated balloon 150A can have any shape, for example and without limitation. As illustrated, as an example, the inflated balloon 150A in this embodiment is a columnar or fully cylindrical at the first location 241 and is partially cylindrical at the second location 242, resulting in a U-shape. However, the inflated balloon 150A also can be other shapes such as a spherical shape, as long as the balloon 150A does not cover or block the second port 115 around the second location 242.

Figure 12:
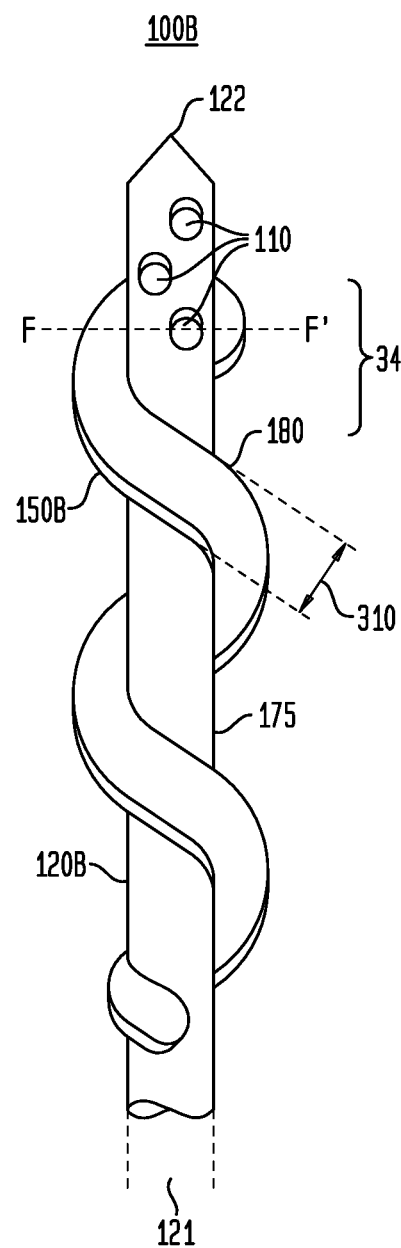
FIG. 12 is a first, partial isometric view illustrating a representative third embodiment of a catheter, such as a dialysis catheter, having a representative third embodiment of a balloon in a second, inflated state or configuration.

FIG. 12 is a first, partial isometric view illustrating a representative third embodiment of a catheter 100B, such as a dialysis catheter, having a representative third embodiment of a balloon 150B in a second, inflated state or configuration. FIG. 13 is a second, partial isometric view illustrating the representative third embodiment of the catheter 100B having the representative third embodiment of the balloon 150B in the second, inflated state or configuration. FIG. 14 is a first, transverse cross-sectional view (in the F-F' plane) illustrating the representative third embodiment of the catheter 100B having the representative third embodiment of the balloon 150B in the second, inflated state or configuration of FIG. 12. FIG. 15 is a second, transverse cross-sectional view (in the G-G' plane) illustrating the representative third embodiment of the catheter 100B having the representative third embodiment of the balloon 150B in the second, inflated state or configuration of FIG. 13. FIG. 16 is a third, transverse cross-sectional view (in the H-H' plane) illustrating the representative third embodiment of the catheter 100B having the representative third embodiment of the balloon 150B in the second, inflated state or configuration of FIG. 13. FIGS. 12 and 13 are shown as partial views of the catheter 100B, without illustrating the connecting tubes 105 and the various lumens and ports, because the catheter 100B includes the same components in the same configuration as previously described for catheter 100, and operates identically to the catheter 100, differing only with respect to the configuration and location of the balloon 150B, as illustrated in the partial views and cross-sectional views. In the interests of brevity, only the differences between the catheter 100B and the catheter 100 and catheter 100A are described.

Referring to FIGS. 12-16, the differences between the catheter 100B and the catheters 100, 100A are also: (1) the configuration of a balloon 150B, as a helical shape which also tapers or diminishes in diameter from the first end 122 to the second end 121 (illustrated in FIGS. 12 and 13); (2) the location of the balloon 150B on the catheter body 120B, as the balloon 150B is wrapped helically (or spiraling) around the catheter body 120B; and (3) a plurality of third ports 140 are included in the catheter body 120B and are coupled to the balloon 150B at multiple locations, as illustrated in the cross-sectional views of FIGS. 14 and 16 taken at different locations along the catheter 100B. The balloon 150B is coupled at least partially surrounding the catheter body 120 between the one or more first ports 110 and the one or more second ports 115 at a first location 341 of the catheter body 120B. The first location 341 extends longitudinally a first predetermined distance 343 between the one or more first ports 110 and the one or more second ports 115. The first end 152 of the balloon 150B also may be partially spherical at the first location 341.

The balloon 150B is further coupled at least partially surrounding the one or more second ports 115 at a second location 342 of the catheter body 120B. The second location 342 extends longitudinally a second predetermined distance 344 between the one or more second ports 115 and the second, proximal end 121. The balloon 150B is helically wrapped along the first and second locations 341, 342. The balloon 150B is helical, and partially surrounds the catheter body 120B at the second location 342. Alternatively, the balloon 150B may be tubular, and wrapped around the catheter body 120B in a helix or spiral configuration.

A diameter of the balloon 150B can be different at the first location 341 and the second location 342. For example, as illustrated in FIGS. 11 and 12, in this embodiment, a first diameter 305 of the balloon 150B at the first location 341 becomes smaller, diminishing to a second diameter 310 at the second location 342, and thereafter either maintaining the second diameter 310 or further tapering in diameter at the second location 342 in an inflated state. As previously discussed, in various representative embodiments, the balloon 150B may be inflated up to (less than or equal to) twice the diameter of the catheter body 120B, for example and without limitation.

FIG. 17 is a flow chart illustrating a method of using a representative embodiment of a catheter 100, 100A, 100B having a representative embodiment of a balloon 150, 150A, 150B, during a dialysis session, and provides a useful summary. Referring to FIG. 17, in preparation, a catheter 100, 100A, 100B has been inserted into the blood vessel of a human or veterinary patient or subject. The method begins, start step 200, by connecting the first and second connecting tubes 105A, 105B to a dialysis machine, step 205, and typically coupling a syringe filled with a biocompatible fluid to the third connecting tube 105C, step 210. The balloon 150, 150A, 150B of the catheter 100, 100A, 100B is inflated, step 215, such as by using a syringe to fill the balloon lumen 170 of the balloon 150, 150A, 150B with a biocompatible fluid such as saline. As an option, the balloon 150, 150A, 150B may be deflated as previously described, step 220. When there will be additional inflations and deflations of the balloon 150, 150A, 150B, step 225, such as may be decided by appropriate medical or veterinary personnel or practitioners, the method returns to step 215 and iterates. When there will not be further additional inflations and deflations of the balloon 150, 150A, 150B, the balloon 150, 150A, 150B is either reinflated, step 230, or left in the inflated state from step 215. Maintaining the balloon 150, 150A, 150B in an inflated state, dialysis of the human or veterinary subject is performed, step 235. When dialysis is completed, the balloon 150, 150A, 150B is deflated, step 240, the syringe is uncoupled from the third connecting tube 105C, step 245, and the first and second connecting tubes 105A, 105B are uncoupled from the dialysis machine, step 250. Then, the method may end, return step 255.

As a result, the use of the catheter 100, 100A, 100B provides significant advantages. The problem of fibrin sheath formation can be mitigated, because the balloon 150, 150A, 150B can be inflated and deflated to break up any formed fibrin sheath which may have covered the one or more first ports 110 and the one or more second ports 115. Therefore, any significant blockage of the one or more first ports 110 and the one or more second ports 115 can be prevented, and which serves to increase the efficiency of dialysis and further reducing the frequency of catheter replacements. In addition, because the inflated balloon 150, 150A, 150B operates as a barrier between the one or more first ports 110 and the one or more second ports 115, the amount of recirculation during dialysis can be reduced as well. Lastly, the inflated balloon 150, 150A, 150B also helps maintain the one or more first ports 110 and the one or more second ports 115 of the catheter 100, 100A, 100B away from the walls of the blood vessel, also increasing the efficiency of dialysis.

As mentioned above, the balloon 150, 150A, 150B is comprised of any suitable flexible (and possibly stretchable), biocompatible material, such as silicones, silicone rubber, latex, polytetrafluoroethylene (PTFE or Teflon), etc., and the catheter 100, 100A, 100B more generally, is comprised of any suitable flexible material, such as a biocompatible or inert polymer or plastic, such as polystyrene or polytetrafluoroethylene (PTFE or Teflon), carbon fiber, or any type of flexible biocompatible material, for example and without limitation. The catheter 100, 100A, 100B also may have one or more coatings (not separately illustrated), such as an antibiotic or antimicrobial coating, for example and without limitation. Other representative examples of biocompatible or inert polymers include, but are not limited to, fluorinated polymers or copolymers such as poly(vinylidene fluoride), poly(vinylidene fluoride-co-hexafluoropropene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-cotrimethylene carbonate); poly(phosphoesters); poly(phosphoester urethane); poly(trimethylene carbonate); poly(iminocarbonate); poly (ethylene); and any derivatives, analogs, homologues, congeners, salts, copolymers and combinations thereof.

The biocompatible or inert polymers may also include, but are not limited to, poly(propylene) copoly(ether-esters) such as, for example, poly(dioxanone) and poly(ethylene oxide)/poly(lactic acid); poly(anhydrides), poly(alkylene oxalates); poly(phosphazenes); poly(urethanes); silicones; silicone rubber; poly(esters); poly(olefins); copolymers of poly(isobutylene); copolymers of ethylene-alphaolefin; vinyl halide polymers and copolymers such as poly(vinyl chloride); poly(vinyl ethers) such as, for example, poly (vinyl methyl ether); poly(vinylidene halides) such as, for example, poly(vinylidene chloride); poly(acrylonitrile); poly(vinyl ketones); poly(vinyl aromatics) such as poly (styrene); poly(vinyl esters) such as poly(vinyl acetate); copolymers of vinyl monomers and olefins such as poly (ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

The biocompatible or inert polymers may further include, but are not limited to, poly(amides) such as Nylon 66 and poly(caprolactam); alkyd resins; poly(carbonates); poly (oxymethylenes); poly(imides); poly(ester amides); poly (ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof. At least one of polymers can be a poly(ester amide), a poly(lactide)

or a poly(lactide-co-glycolide) copolymer; and any derivatives, analogs, homologues, congeners, salts, copolymers and combinations thereof.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. In addition, every intervening sub-range within range is contemplated, in any combination, and is within the scope of the disclosure. For example, for the range of 5-10, the sub-ranges 5-6, 5-7, 5-8, 5-9, 6-7, 6-8, 6-9, 6-10, 7-8, 7-9, 7-10, 8-9, 8-10, and 9-10 are contemplated and within the scope of the disclosed range.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

It is claimed:

1. A catheter, comprising:
   a catheter body having a first, distal end and a second, proximal end, the catheter body comprising:
   a plurality of ports, the plurality of ports comprising one or more first ports, one or more second ports, and at least one third port, all of the one or more first ports arranged at or spaced apart proximally from the first end, all of the one or more second ports arranged spaced apart longitudinally and proximally from all of the one or more first ports, all of the one or more second ports further offset transversely from all of the one or more first ports and arranged on an opposite side of the catheter body from all of the one or more first ports; and
   a plurality of lumens, the plurality of lumens comprising a first lumen, a second lumen, and a third lumen, the first lumen in fluid communication with the one or more first ports, the second lumen in fluid communication with the one or more second ports, and the third lumen in fluid communication with the at least one third port;

and
   a balloon coupled circumferentially to and surrounding the catheter body at a first location both proximal to all of the one or more first ports and distal to all of the one or more second ports.

2. The catheter of claim 1, wherein the balloon comprises a balloon lumen, and the balloon is coupled to the at least one third port, with the third lumen in fluid communication with the at least one third port and the balloon lumen.

3. The catheter of claim 1, wherein the balloon is further coupled at a second location of the catheter body, the second location transversely surrounding the one or more second ports and the second end.

4. The catheter of claim 3, wherein the balloon is further coupled at a second location of the catheter body, the second location extending longitudinally between the one or more second ports and the second end.

5. The catheter of claim 4, wherein the balloon is coupled helically around the catheter body at the second location.

6. The catheter of claim 5, wherein in an inflated state, the balloon comprises a first diameter at the first location and a second diameter at the second location, the first diameter greater than the second diameter.

7. The catheter of claim 1, wherein a diameter of the balloon in an inflated state is user-selectable.

8. The catheter of claim 1, further comprising:
   a hub coupled to the second end of the catheter body; and
   a plurality of connecting tubes coupled to the hub, the plurality of connecting tubes comprising a first connecting tube in fluid communication with the first lumen, a second connecting tube in fluid communication with the second lumen, and a third connecting tube in fluid communication with the third lumen.

9. A method of using a catheter of claim 8 for dialysis, the catheter having been inserted into a blood vessel of a human or veterinary subject, the method comprising:
   coupling the first and second connecting tubes to a dialysis machine;
   inflating the balloon of the catheter; and
   while the balloon is inflated, performing dialysis of the human or veterinary subject.

10. The method of using a catheter of claim 9, further comprising:
   prior to performing dialysis, repeatedly inflating and deflating the balloon.

11. The method for using a catheter of claim 9, wherein after performing dialysis of the human subject, the method further comprises:
   deflating the balloon of the catheter; and
   disconnecting the first and second connecting tubes from the dialysis machine.

12. The method for using a catheter of claim 9, wherein the step of inflating the balloon further comprises:
   coupling a syringe to the third connecting tube, the syringe filled with a biocompatible fluid; and
   using the syringe, injecting the biocompatible fluid into the third connecting tube to inflate the balloon.

13. A dialysis catheter, comprising:
   a catheter body having a first, distal end and a second, proximal end, the catheter body comprising:
      a plurality of ports, the plurality of ports comprising one or more first ports, one or more second ports, and at least one third port, all of the one or more first ports arranged at or spaced apart proximally from the first end, all of the one or more second ports arranged spaced apart longitudinally and proximally from all of the one or more first ports, all of the one or more second ports further offset transversely from all of the one or more first ports and arranged on an opposite side of the catheter body from all of the one or more first ports; and
      a plurality of lumens, the plurality of lumens comprising a first lumen, a second lumen, and a third lumen, the first lumen in fluid communication with the one or more first ports, the second lumen in fluid communication with the one or more second ports;
   and
   a balloon having a balloon lumen, the balloon coupled circumferentially to and surrounding the catheter body at a first location, the first location both proximal to all of the one or more first ports and distal to all of the one or more second ports, the balloon further coupled to the at least one third port, with the third lumen in fluid communication with the at least one third port and the balloon lumen.

14. The dialysis catheter of claim 13, wherein the balloon is further coupled helically around the catheter body at a second location between the one or more second ports and the second end of the catheter body.

15. The dialysis catheter of claim 13, further comprising:
   a hub coupled to the second end of the catheter body; and
   a plurality of connecting tubes coupled to the hub, the plurality of connecting tubes comprising a first connecting tube in fluid communication with the first lumen, a second connecting tube in fluid communication with the second lumen, and a third connecting tube in fluid communication with the third lumen, the third connecting tube configured with a connector to mate with a luer lock tip of a syringe.

16. A dialysis catheter, comprising:
   a catheter body having a first, distal end and a second, proximal end, the catheter body comprising:
      a plurality of ports, the plurality of ports comprising a plurality of first ports, a plurality of second ports, and at least one third port, all of the plurality of first ports of first port arranged at or spaced apart proximally from the first end on a first side of the catheter body, all of the plurality of second ports arranged spaced apart longitudinally and proximally from all of the plurality of first ports, and all of the plurality of second ports further arranged spaced apart transversely from all of the plurality of first ports on a second, opposite side of the catheter body; and
      a plurality of lumens, the plurality of lumens comprising a first lumen, a second lumen, and a third lumen, the first lumen in fluid communication with the plurality of first ports, the second lumen in fluid communication with the plurality of second ports;
   and
   a balloon having a balloon lumen, the balloon coupled circumferentially to and surrounding the catheter body at a first location, the first location both proximal to all of the one or more first ports and distal to all of the one or more second ports, the balloon further coupled at a second location of the catheter body, the second location extending proximally from the first location and transversely surrounding all of the plurality of second ports, the balloon further coupled to the at least one third port, with the third lumen in fluid communication with the at least one third port and the balloon lumen.

* * * * *